(12) United States Patent
Konno

(10) Patent No.: US 9,241,611 B2
(45) Date of Patent: Jan. 26, 2016

(54) TRACK-FORMING DEVICE

(71) Applicant: OLYMPUS CORPORATION, Tokyo (JP)

(72) Inventor: Osamu Konno, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 43 days.

(21) Appl. No.: 14/109,142

(22) Filed: Dec. 17, 2013

(65) Prior Publication Data

US 2014/0107420 A1  Apr. 17, 2014

Related U.S. Application Data

(63) Continuation of application No. PCT/JP2012/064563, filed on Jun. 6, 2012.

(30) Foreign Application Priority Data

Jun. 23, 2011 (JP) .................. 2011-139782

(51) Int. Cl.
*A61B 1/04* (2006.01)
*A61B 1/00* (2006.01)
*A61B 1/005* (2006.01)
*A61B 1/31* (2006.01)

(52) U.S. Cl.
CPC ........... *A61B 1/00158* (2013.01); *A61B 1/0055* (2013.01); *A61B 1/0057* (2013.01); *A61B 1/00149* (2013.01); *A61B 1/00154* (2013.01); *A61B 1/31* (2013.01)

(58) Field of Classification Search
USPC ................... 600/114, 139, 141–142, 145–146
See application file for complete search history.

(56) References Cited

U.S. PATENT DOCUMENTS

| | | | | | |
|---|---|---|---|---|---|
| 5,174,276 | A | * | 12/1992 | Crockard | 600/104 |
| 5,251,611 | A | * | 10/1993 | Zehel et al. | 600/141 |
| 5,337,733 | A | * | 8/1994 | Bauerfeind et al. | 600/139 |
| 5,482,029 | A | * | 1/1996 | Sekiguchi et al. | 600/109 |
| 5,749,828 | A | * | 5/1998 | Solomon et al. | 600/141 |
| 5,759,151 | A | * | 6/1998 | Sturges | 600/146 |
| 5,916,147 | A | * | 6/1999 | Boury | 600/146 |

(Continued)

FOREIGN PATENT DOCUMENTS

| | | |
|---|---|---|
| JP | Sho 58-101601 U | 7/1983 |
| JP | 06-022905 A | 2/1994 |

(Continued)

OTHER PUBLICATIONS

International Search Report dated Sep. 11, 2012 issued in PCT/JP2012/064563.

*Primary Examiner* — Matthew J Kasztejna
(74) *Attorney, Agent, or Firm* — Scully, Scott, Murphy & Presser, P.C.

(57) ABSTRACT

A track-forming device can form an insertion route (track) along which a treatment tool is easily inserted. The track-forming device includes: a plurality of track-forming segmented members that are arranged in the longitudinal direction with spaces therebetween; a soft wire that connects the plurality of track-forming segmented members; and a wire pulling section that brings the plurality of track-forming segmented members into contact with each other in the longitudinal direction. When the plurality of track-forming segmented members are brought into contact with each other by the wire pulling section, a predetermined track is formed.

3 Claims, 18 Drawing Sheets

(56) References Cited

U.S. PATENT DOCUMENTS

| | | | |
|---|---|---|---|
| 6,790,173 B2 * | 9/2004 | Saadat et al. | 600/114 |
| 6,800,056 B2 * | 10/2004 | Tartaglia et al. | 600/114 |
| 6,858,005 B2 * | 2/2005 | Ohline et al. | 600/141 |
| 8,298,161 B2 * | 10/2012 | Vargas | 600/587 |
| 8,834,354 B2 * | 9/2014 | Belson | 600/114 |
| 2006/0058582 A1 * | 3/2006 | Maahs et al. | 600/144 |
| 2009/0182268 A1 | 7/2009 | Thielen et al. | |
| 2011/0046442 A1 | 2/2011 | Matsushita | |

FOREIGN PATENT DOCUMENTS

| | | |
|---|---|---|
| JP | 2007-511247 A | 5/2007 |
| JP | 2008-541036 A | 11/2008 |
| JP | 2009-528890 A | 8/2009 |
| JP | 2010-360 A | 1/2010 |
| JP | 2011-036601 A | 2/2011 |
| WO | 2004/103430 A2 | 12/2004 |
| WO | WO 2006/117519 A1 | 11/2006 |
| WO | 2007/103161 A2 | 9/2007 |

* cited by examiner

TRACK-FORMING DEVICE

CROSS-REFERENCE TO RELATED APPLICATIONS

This is a continuation of International Application PCT/JP2012/064563, with an international filing date of Jun. 6, 2012, which is hereby incorporated by reference herein in its entirety. This application is based on Japanese Patent Application No. 2011-139782, the contents of which are incorporated herein by reference.

TECHNICAL FIELD

The present invention relates to a track-forming device that forms an insertion route (track) in a body cavity when a soft endoscope or a soft sheath is inserted into the body cavity, in order to improve the ease of insertion thereof into the body cavity.

BACKGROUND ART

An endoscope that is formed of a flexible tube portion and a handle portion, in which a shape-memory alloy is disposed in the flexible tube of the endoscope, and a heating wire (transformation temperature medium means) for heating the shape-memory alloy to a transformation temperature is provided, has been conventionally known (for example, see Patent Literature (PTL) 1).

CITATION LIST

Patent Literature

{PTL 1}
Japanese Unexamined Utility Model Application, Publication No. Sho 58-101601

SUMMARY OF INVENTION

Technical Problem

In the endoscope disclosed in PTL 1, in order to improve the ease of insertion of the endoscope, when the endoscope is moved forward to a bent portion in the large intestine, for example, the shape-memory alloy is heated to the transformation temperature in the bent portion of the large intestine, thereby correcting the shape of the endoscope to a straight shape to allow insertion of the endoscope itself.

According to the endoscope disclosed in PTL 1, the original shape of tissue (intestine, kidney, or heart) needs to be greatly changed in order to ensure an insertion route of the treatment tool, thereby making it impossible to easily insert the treatment tool.

The present invention provides a track-forming device capable of forming an insertion route (track) along which the treatment tool can be easily inserted.

Solution to Problem

One aspect of the present invention is a track-forming device including: a plurality of track-forming segmented members that are arranged in the longitudinal direction with spaces therebetween; a soft connecting member that connects the plurality of track-forming segmented members; and a contacting section that brings the plurality of track-forming segmented members into contact with each other in the longitudinal direction, in which, when the plurality of track-forming segmented members are brought into contact with each other by the contacting section, a predetermined track is formed.

According to the above-described aspect, while the contacting section is not actuated, the plurality of track-forming segmented members that are arranged in the longitudinal direction with spaces therebetween are connected by the soft connecting member so as to be able to be curved. In this state, when the track-forming device of the above-described aspect is inserted into a tubular insertion section, which is formed of a soft member, of an endoscope or a sheath, for example, the track-forming device can be inserted into the insertion section so as to conform to the shape of the insertion section. In this state, the tubular insertion section is inserted into the body cavity. Because both the tubular insertion section and the track-forming device of the above-described aspect can be curved in this state, they are inserted into the body cavity while deforming to conform to the internal shape of the body cavity.

Then, when the contacting section is actuated, the plurality of track-forming segmented members are brought into contact with each other by the contacting section, thereby forming a predetermined track conforming, for example, to the internal shape of the body cavity. Thus, the tubular insertion section, which is formed of a soft member, is deformed to conform to the shape of the track-forming device of the above-described aspect, that is, the above-described predetermined track. In this state, the tubular insertion section is pushed further into the body cavity. Thus, the tubular insertion section is inserted into the body cavity along the predetermined track formed by the track-forming device of the above-described aspect.

By doing so, it is possible to insert the tubular insertion section so as to conform to the internal shape of the body cavity without deforming the tissue in the body cavity. Specifically, with the above-described aspect, it is possible to form an insertion route (track) along which the insertion section is easily inserted and to easily insert the insertion section into the body cavity along this insertion route.

In the above-described aspect, tapers having predetermined angles may be formed on contact faces of the track-forming segmented members.

With this structure, the plurality of track-forming segmented members are brought into contact with each other by the contacting section, thereby bringing the contact faces of the track-forming segmented members, on which the tapers are formed, into contact with each other and forming a predetermined track conforming, for example, to the internal shape of the body cavity. Note that a three-dimensional track can be formed by providing tapers on the top face and the side face, i.e., in two directions.

In the above-described aspect, the connecting member may be a soft wire that is inserted into all the track-forming segmented members in the longitudinal direction and that is secured to one of the track-forming segmented members that is located at a distal end; and the contacting section may be a wire pulling section that pulls the wire toward a base end.

With this structure, when the soft wire inserted into all the track-forming segmented members is pulled toward the base end by the wire pulling section, the plurality of track-forming segmented members can be brought into contact with each other, thus forming a predetermined track conforming, for example, to the internal shape of the body cavity.

In the above-described aspect, each of the track-forming segmented members may have, at one end portion thereof, a wire locking unit that locks the wire and have, at the other end portion thereof, a wire unlocking unit that unlocks the wire by being engaged with the wire locking unit of an adjacent one of the track-forming segmented members.

With this structure, when the soft wire inserted into all the track-forming segmented members is pulled toward the base end by the wire pulling section, the lock on the wire can be released by engaging the wire locking unit, which is formed at one end portion of each of the track-forming segmented members, with the wire unlocking unit, which is formed at the other end portion thereof.

In the above-described aspect, locking forces of the wire locking units of the track-forming segmented members that are located closer to the base end may be set smaller than locking forces of the wire locking units of the track-forming segmented members that are located closer to the distal end.

With this structure, when the soft wire inserted into all the track-forming segmented members is pulled toward the base end by the wire pulling section, the track-forming segmented members can be brought into contact sequentially starting from the base end, thus forming a predetermined track. By forming the track sequentially starting from the base end in this way, the ease of insertion of the tubular insertion section into the body cavity can be improved.

In the above-described aspect, external thread portions may be formed at predetermined positions on the wire; and internal thread portions to be engaged with the external thread portion may be formed on internal sides of the track-forming segmented members.

With this structure, when the soft wire inserted into all the track-forming segmented members is rotated about the axis, the external thread portions formed at the predetermined positions on the wire can be engaged with the internal thread portions formed on the internal sides of the track-forming segmented members, thus bringing the plurality of track-forming segmented members into contact with each other and forming a predetermined track conforming, for example, to the internal shape of the body cavity.

In the above-described aspect, the external thread portions that are located closer to the base end of the wire may be formed shorter in the longitudinal direction than the external thread portions that are located closer to the distal end thereof.

With this structure, when the soft wire inserted into all the track-forming segmented members is rotated about the axis, the track-forming segmented members can be brought into contact with each other sequentially starting from the base end, thus forming a predetermined track. By forming the track sequentially starting from the base end in this way, the ease of insertion of the tubular insertion section into the body cavity can be improved.

In the above-described aspect, the track-forming segmented members may be made of a magnetic material; and the contacting section may be a magnetic force generator that brings the plurality of track-forming segmented members into contact with each other in the longitudinal direction due to a magnetic force.

With this structure, it is possible to bring the plurality of track-forming segmented members into contact with each other in the longitudinal direction due to a magnetic force and to form a predetermined track in a non-contact manner.

In the above-described aspect, a plurality of the magnetic force generators may be arranged along a direction in which the track-forming segmented members are arranged, and the magnetic force generators may generate magnetic forces sequentially starting from the base end.

With this structure, a magnetic force can be applied to the track-forming segmented members sequentially starting from the base end, thus forming a predetermined track. By forming the track sequentially starting from the base end in this way, the ease of insertion of the tubular insertion section into the body cavity can be improved.

Advantageous Effects of Invention

According to the present invention, an advantageous effect is afforded in that an insertion route (track) along which a treatment tool is easily inserted can be formed.

BRIEF DESCRIPTION OF DRAWINGS

FIG. 7(a) shows a natural state of the large intestine; FIG. 7(b) shows a state in which the insertion section has been inserted into the large intestine; FIG. 7(c) shows a state in which the track-forming device has been inserted into the insertion section; FIG. 7(d) shows a state in which the track-forming device in the insertion section has formed a track; and FIG. 7(e) shows a state in which the insertion section is inserted into the large intestine along the track of the track-forming device.

FIG. 8(a) shows a state in which the insertion section has been inserted into the large intestine; FIG. 8(b) shows a state in which the track-forming device has been removed from the insertion section; FIG. 8(c) shows a state in which a new track-forming device has been inserted into the insertion section; FIG. 8(d) shows a state in which the track-forming device in the insertion section has formed a track; and FIG. 8(e) shows a state in which the insertion section is inserted into the large intestine along the track of the track-forming device.

FIG. 9(a) is an overall view; FIG. 9(b) is a side view of a track-forming segmented member, and FIG. 9(c) is a top view of the track-forming segmented member.

FIG. 17(a) is a front view thereof when viewed from the base end; FIG. 17(b) is a longitudinal sectional view thereof; and FIG. 17(c) is a front view thereof when viewed from the distal end.

FIG. 29(a) shows a state in which the insertion section has been inserted into the pericardial cavity; FIG. 29(b) shows a state in which the track-forming device in the insertion section forms a track sequentially starting from the base end; FIG. 29(c) shows a state in which the track-forming device in the insertion section further forms the track sequentially starting from the base end; and FIG. 29(d) shows a state in which the insertion section is inserted into the pericardial cavity along the track of the track-forming device.

FIG. 30(a) is a side view thereof (soft state); and FIG. 30(b) is a longitudinal sectional view of a track-forming segmented member.

DESCRIPTION OF EMBODIMENTS

First Embodiment

A track-forming device 1 according to a first embodiment of the present invention will be described below with reference to the drawings.

Figure 1:
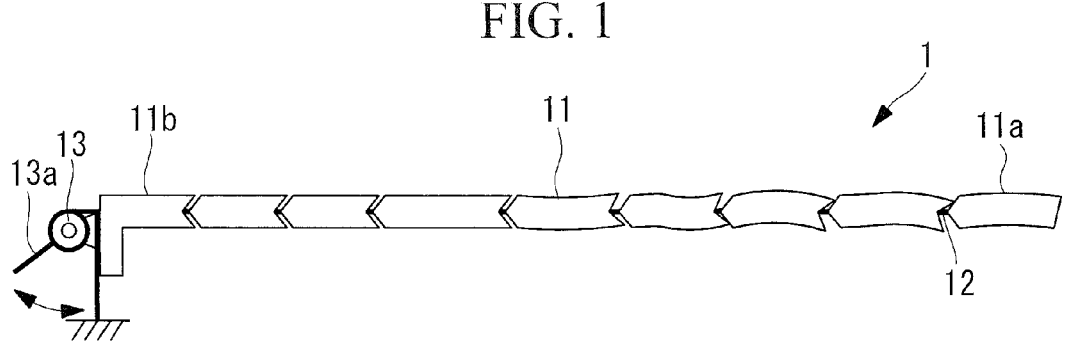
FIG. 1 is a side view of a track-forming device according to a first embodiment of the present invention (soft state).

As shown in FIG. 1, the track-forming device 1 of this embodiment is to be inserted into a tubular insertion section formed of a soft member and includes a plurality of track-forming segmented members 11 that are arranged in the longitudinal direction with spaces therebetween, a soft wire (connecting member) 12 that connects the plurality of track-forming segmented members 11, and a wire pulling section (contacting section) 13 that pulls the wire 12 toward a base end.

Figure 2:
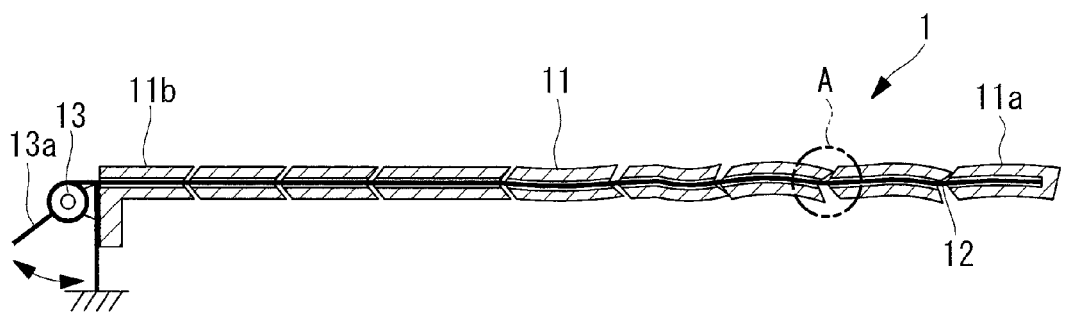
FIG. 2 is a longitudinal sectional view of the track-forming device shown in FIG. 1.

As shown in FIG. 2, the track-forming segmented members 11 are tubular members having longitudinally-formed holes into which the wire 12 is inserted. The track-forming segmented members 11 are brought into contact with each other in the longitudinal direction when the wire pulling section 13 pulls the wire 12 toward the base end. V-shaped tapers having predetermined angles are formed on contact faces of the track-forming segmented members 11 (for example, in a portion A shown in FIG. 2). With this structure, the track-forming segmented members 11 are brought into contact with each other in the longitudinal direction, thereby bringing the V-shaped tapers having the predetermined angles into contact and forming a predetermined track.

Note that these V-shaped tapers prevent the adjacent track-forming segmented members 11 from relatively rotating about their axes when the plurality of track-forming segmented members 11 are brought into contact with each other; however, the shapes of the contact faces of the track-forming segmented members 11 are not limited thereto, and any shapes can be adopted as long as they can prevent relative rotation of the adjacent track-forming segmented members 11 about their axes.

The wire 12 is a soft wire inserted into all the track-forming segmented members 11 in the longitudinal direction, a first end of the wire 12 is secured to a distal-end track-forming segmented member 11a, and a second end of the wire 12 is secured to the wire pulling section 13.

The wire pulling section 13 is, for example, a drum-type winding device that winds up the wire 12 and is secured to a base-end track-forming segmented member 11b. When a handle 13a is actuated, the wire pulling section 13 winds up the wire 12 so as to pull the wire 12 toward the base end.

Figure 3:
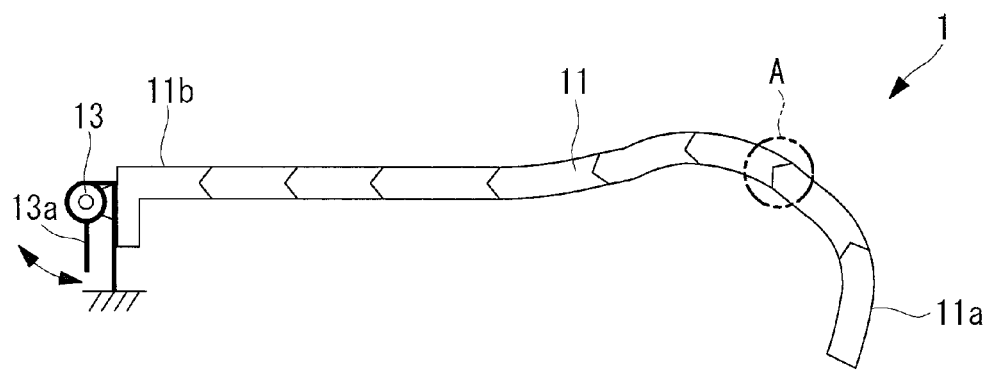
FIG. 3 is a side view of the track-forming device shown in FIG. 1 (track forming state).

By actuating the wire pulling section 13, the wire 12 and the distal-end track-forming segmented member 11a secured to the first end of the wire 12 are pulled toward the base end. Thus, as shown in FIG. 3, the plurality of track-forming segmented members 11 are brought into contact with each other in the longitudinal direction, thus forming a predetermined track.

The operation of the track-forming device 1 of this embodiment, having the above-described structure, will be described below.

Figure 4:
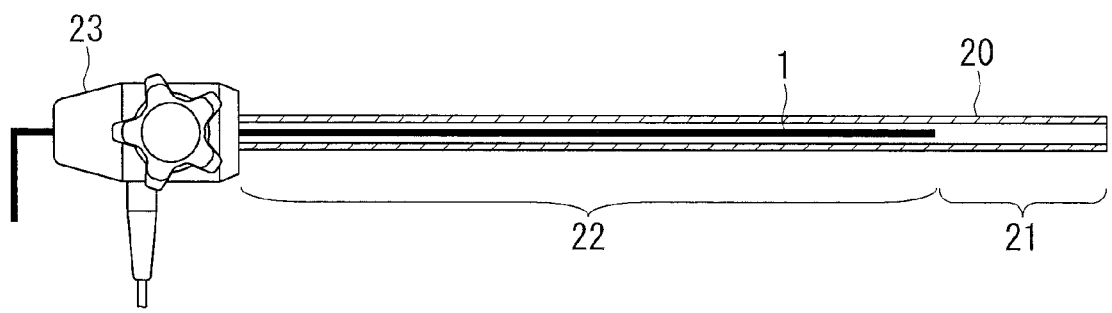
FIG. 4 is a view showing a state in which the track-forming device shown in FIG. 1 has been inserted into an insertion section of an endoscope.

As shown in FIG. 4, the track-forming device 1 of this embodiment is inserted into a tubular insertion section 20, formed of a soft member, of an endoscope, for example.

The insertion section 20 has a channel into which the track-forming device 1 of this embodiment is inserted in the longitudinal direction, and the track-forming device 1 is inserted into the channel. The insertion section 20 is formed of, in order from the distal end, a bendable distal-end bending portion 21, a flexible portion 22 having flexibility, and an operating portion 23 that operates the bending action of the distal-end bending portion 21.

Figure 5:
FIG. 5 is an overall view showing a soft state of the track-forming device shown in FIG. 1.

In the track-forming device 1 of this embodiment, while the wire pulling section 13 is not actuated, as shown in FIG. 1, the plurality of track-forming segmented members 11 that are arranged in the longitudinal direction with spaces therebetween are connected by the soft wire 12 so as to be able to be curved. FIG. 5 is a schematic diagram showing this state. In this state, when the track-forming device 1 of this embodiment is inserted into the insertion section 20, the track-forming device 1 can be inserted in the insertion section 20 so as to conform to the shape of the insertion section 20. In this state, the insertion section 20 is inserted into the body cavity. Because both the insertion section 20 and the track-forming device 1 of this embodiment can be curved in this state, the insertion section 20 and the track-forming device 1 are inserted into the body cavity while deforming to conform to the internal shape of the body cavity.

Figure 6:
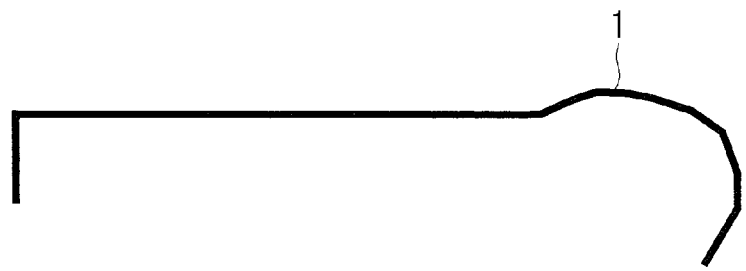
FIG. 6 is an overall view showing a track forming state of the track-forming device shown in FIG. 1.

Then, when the wire pulling section 13 is actuated, as shown in FIG. 3, the plurality of track-forming segmented members 11 are brought into contact with each other by the wire pulling section 13, thereby forming a predetermined track conforming, for example, to the internal shape of the body cavity. FIG. 6 is a schematic diagram showing this state. Thus, the insertion section 20, which is formed of a soft member, is deformed to conform to the shape of the track-forming device 1 of this embodiment, that is, the predetermined track conforming to the internal shape of the body cavity. In this state, the insertion section 20 is pushed further into the body cavity. Thus, the insertion section 20 is inserted into the body cavity along the predetermined track formed by the track-forming device 1 of this embodiment.

Here, if the curvature of the track-forming device 1 exceeds the maximum curvature of the insertion section 20, when the track-forming device 1 forms the track, sliding resistance is increased due to friction between the track-forming device 1 and the channel of the insertion section 20, which may cause a lock state. Therefore, the maximum curvature of the entire shape when the track-forming device 1 forms the track should be smaller than the maximum curvature of the channel of the insertion section 20.

Furthermore, in the soft state of the track-forming device 1, the natural flexibility of the insertion section 20 needs to be ensured. Therefore, in the soft state of the track-forming device 1, the track-forming device 1 and the insertion section 20 should not restrain each other at the maximum curvature of the insertion section 20. Specifically, the inner diameter of the channel of the insertion section 20, the outer diameters of the constituent members of the track-forming device 1, the maximum curvature of the channel of the insertion section 20, and the curvatures of the constituent members of the track-forming device 1 are designed so as to satisfy the above-described conditions.

Note that the track is not necessarily formed for the entire insertion section 20, and the flexibility of a hand side (the base end) thereof may be ensured when the track is formed for the insertion section 20. Furthermore, the target application of the track-forming device 1 of this embodiment is not limited to the insertion section 20 of the endoscope, and the track-forming device 1 of this embodiment may be applied to a sheath.

Next, an operation performed when the insertion section 20 is inserted into the body cavity by using the track-forming device 1 of this embodiment will be described below. Here, a description will be given of an example case in which the insertion section 20 is inserted into the large intestine.

Figure 7:
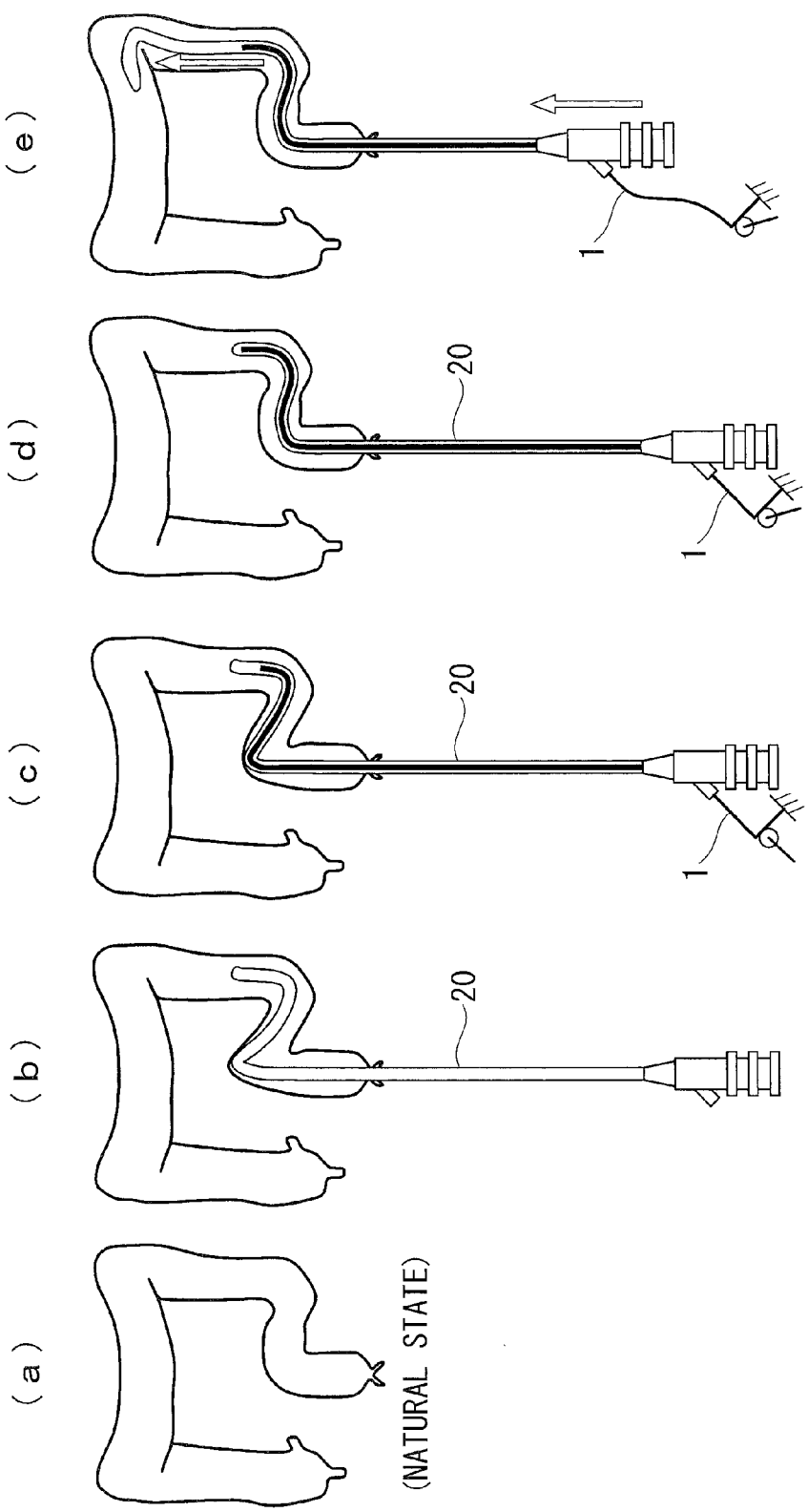
FIG. 7 includes views showing states in which the insertion section is inserted into a large intestine by using the track-forming device shown in FIG. 1, where

FIG. 7(*a*) shows a natural state of the large intestine.

FIG. 7(*b*) shows a state in which the insertion section 20 is inserted into the large intestine to some extent. In this state, the insertion section 20 pushes the large intestine a little in a bent portion of the large intestine.

Next, as shown in FIG. 7(*c*), the track-forming device 1 in the soft state is inserted into the channel of the insertion section 20. Note that, at the time when the insertion section 20 is inserted into the large intestine, the track-forming device 1 in the soft state may be inserted into the channel of the insertion section 20 in advance.

Next, as shown in FIG. 7(*d*), the wire pulling section 13 is actuated to bring the track-forming segmented members 11 of the track-forming device 1 into contact with each other, thus forming a predetermined track. In this state, the track-forming device 1 and the insertion section 20 are formed into a predetermined shape, specifically, a shape conforming to the natural state of the large intestine, thus minimizing the force placed on the large intestine by the insertion section 20.

Next, as shown in FIG. 7(*e*), the insertion section 20 is further inserted while the track-forming device 1 forms the predetermined track. By doing so, the insertion section 20 is inserted while conforming to the shape of the natural state of the large intestine; therefore, it is possible to minimize deformation of the large intestine and to reduce the burden imposed on the large intestine.

Figure 8:
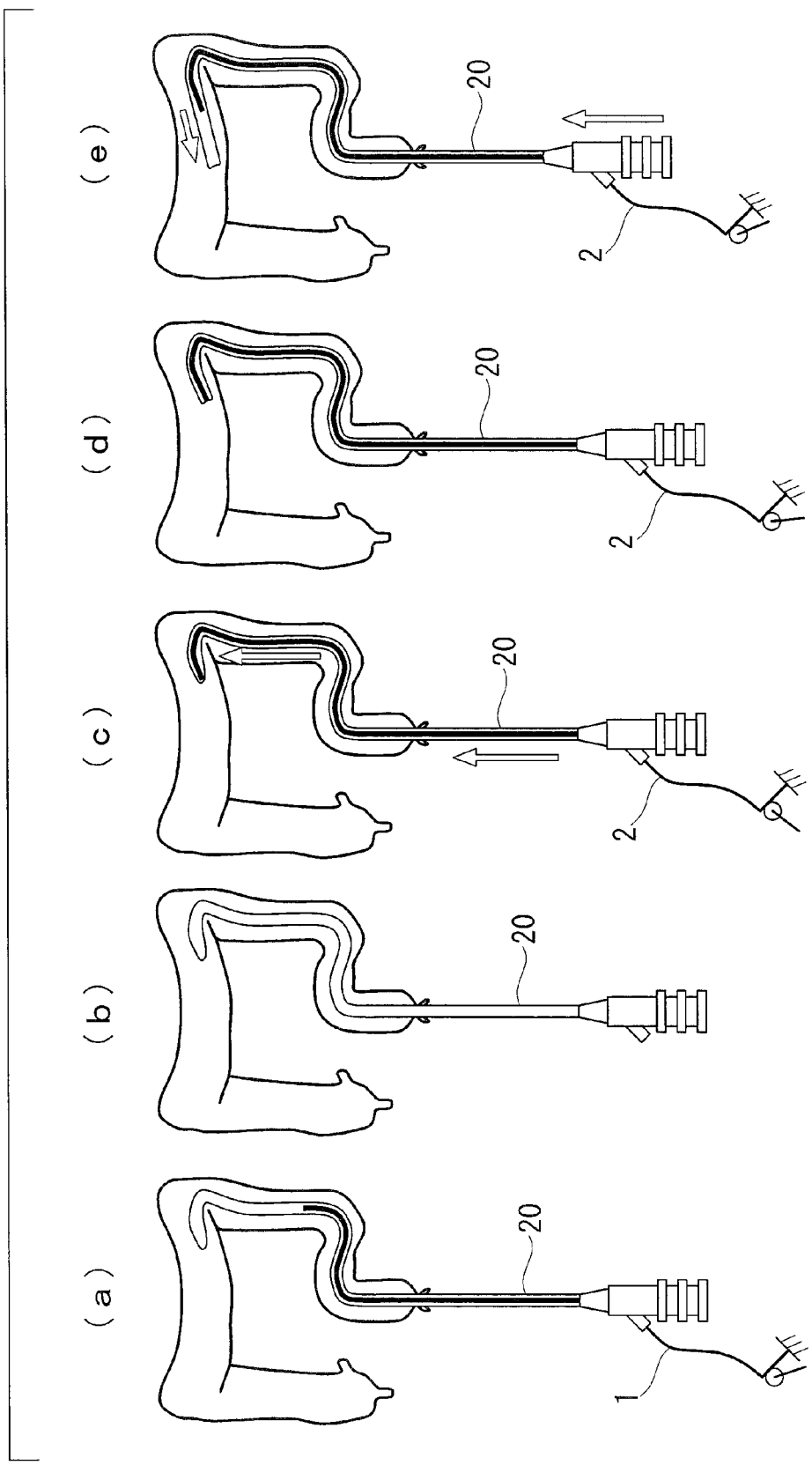
FIG. 8 includes views showing states in which the insertion section is inserted into the large intestine by using the track-forming device shown in FIG. 1, where

FIG. 8(*a*) shows a state in which the insertion section 20 is further inserted while the track-forming device 1 forms the predetermined track.

Next, as shown in FIG. 8(*b*), the track-forming device 1 is softened and removed from the insertion section 20.

Next, as shown in FIG. 8(*c*), a track-forming device 2 that has the same structure as the track-forming device 1 and that forms a track different from that of the track-forming device 1 is inserted into the channel of the insertion section 20 while the track-forming device 2 is in a soft state. At this time, the track-forming device 2 is inserted up to the vicinity of the distal end of the insertion section 20.

Next, as shown in FIG. 8(*d*), the wire pulling section 13 of the track-forming device 2 is actuated to make the track-forming device 2 form a predetermined track. Thus, the track-forming device 2 is formed into a shape conforming to the natural state of the large intestine, thus minimizing the force placed on the large intestine by the insertion section 20.

Next, as shown in FIG. 8(*e*), the insertion section 20 is further inserted while the track-forming device 2 forms the predetermined track. By doing so, the insertion section 20 is inserted while conforming to the shape of the natural state of the large intestine; therefore, it is possible to minimize deformation of the large intestine and to reduce the burden imposed on the large intestine.

The above-described operation is performed by using not only the track-forming devices 1 and 2 but also a track-forming device that forms a track different from those of the track-forming devices 1 and 2, thereby allowing the insertion section 20 to be easily inserted to a deeper portion in the large intestine.

As described above, according to the track-forming device 1 of this embodiment, it is possible to insert the insertion section 20 so as to conform to the internal shape of the body cavity without deforming the tissue in the body cavity. Specifically, with the track-forming device 1 of this embodiment, it is possible to form an insertion route (track) along which the insertion section 20 is easily inserted without imposing an excessive burden on the tissue in the body cavity and to easily insert the insertion section 20 into the body cavity along this insertion route.

Note that, in the track-forming device 1 of this embodiment, the insertion section 20 can be easily inserted into the body cavity by preparing particular shape types depending on the insertion distance of the insertion section 20 and observation sites.

Second Embodiment

Figure 9:
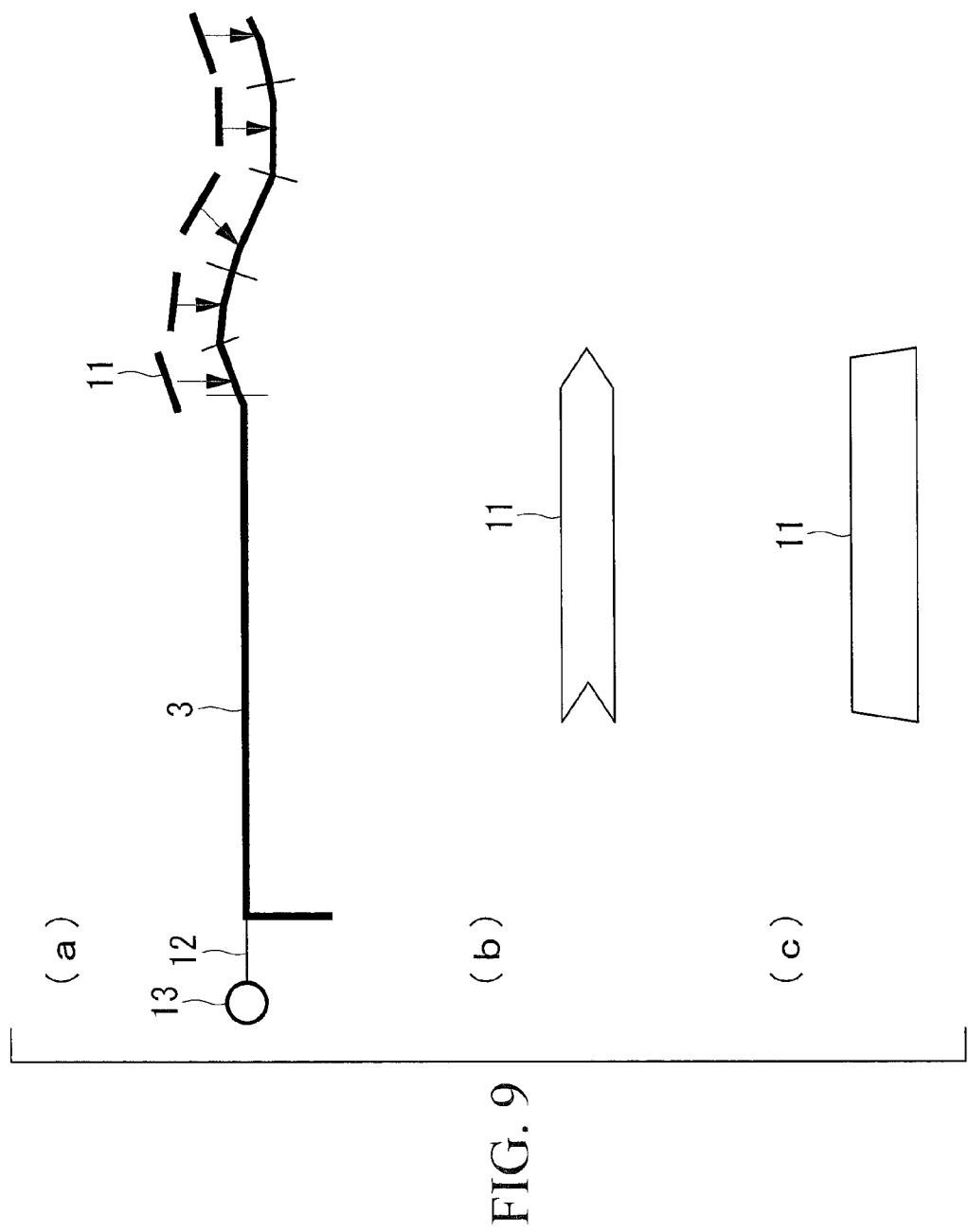
FIG. 9 includes views showing, in outline, the structure of a track-forming device according to a second embodiment of the present invention, where

Next, a track-forming device according to a second embodiment of the present invention will be described below mainly with reference to FIGS. 9 to 11. A track-forming device 3 of this embodiment will be described below mainly in terms of the differences from the track-forming device 1 of the first embodiment, identical symbols are assigned to similarities, and a description thereof will be omitted.

In the track-forming device 3 of this embodiment, as shown in FIG. 9(b), when viewed from a lateral side, a V-shaped taper having a predetermined angle is formed on the contact faces of each track-forming segmented member 11, as in the first embodiment. Furthermore, as shown in FIG. 9(c), when viewed from above, a taper having a predetermined angle is formed on the contact faces thereof.

With this structure, when the track-forming segmented members 11 are brought into contact with each other in the longitudinal direction, a three-dimensional predetermined track conforming to the internal shape of the body cavity is formed.

The operation of the track-forming device 3 of this embodiment, having the above-described structure, will be described below.

Figure 10:
FIG. 10 is a top view of the track-forming device shown in FIG. 9 (soft state).

In the track-forming device 3 of this embodiment, while the wire pulling section 13 is not actuated, as shown in FIG. 10, the plurality of track-forming segmented members 11 that are arranged in the longitudinal direction with spaces therebetween are connected by the soft wire 12 so as to be able to be curved. In this state, when the track-forming device 3 of this embodiment is inserted into the insertion section 20, the track-forming device 3 can be inserted into the insertion section 20 so as to conform to the shape of the insertion section 20. In this state, the insertion section 20 is inserted into the body cavity. Because both the insertion section 20 and the track-forming device 3 of this embodiment can be curved in this state, the insertion section 20 and the track-forming device 3 are inserted into the body cavity while deforming to conform to the internal shape of the body cavity.

Figure 11:
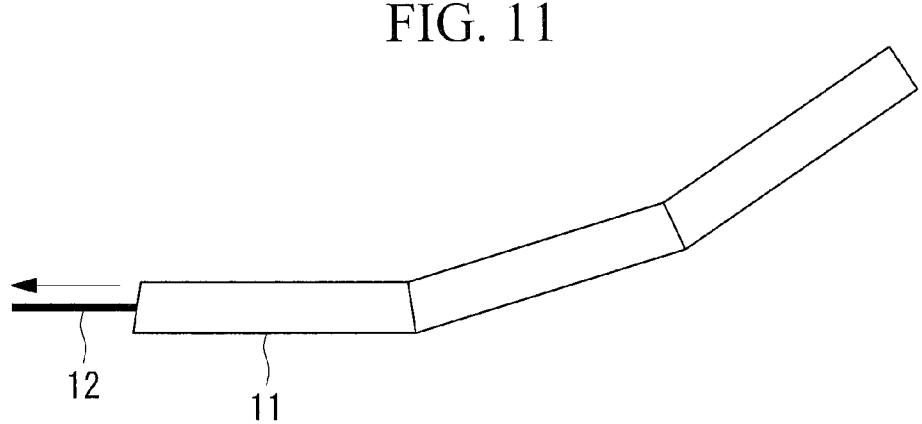
FIG. 11 is a top view of the track-forming device shown in FIG. 9 (track forming state).
Figure 12:
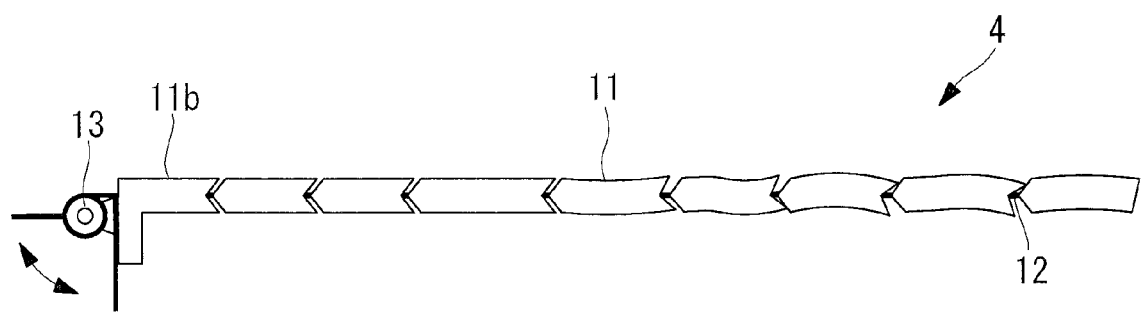
FIG. 12 is a side view of a track-forming device according to a third embodiment of the present invention (soft state).
Figure 13:
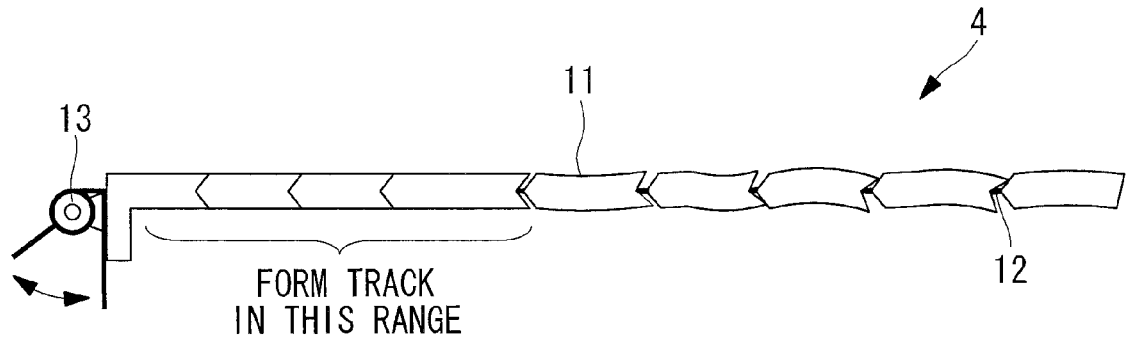
FIG. 13 is a view showing a state in which the track-forming device shown in FIG. 12 is forming a track.
Figure 14:
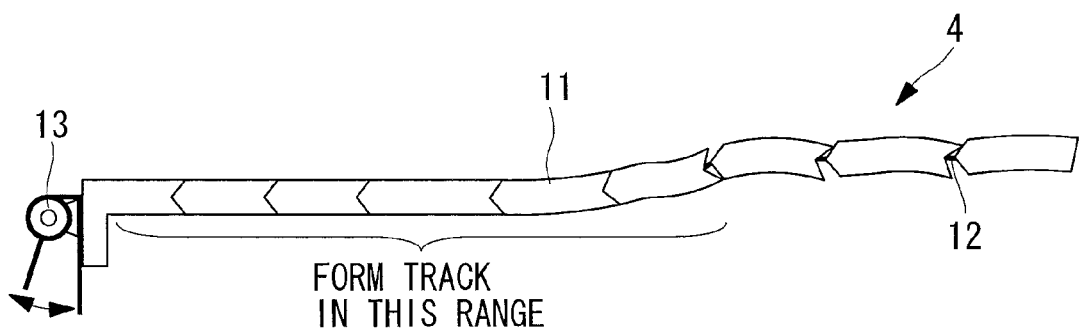
FIG. 14 is a view showing a state in which the track-forming device shown in FIG. 12 is forming the track.
Figure 15:
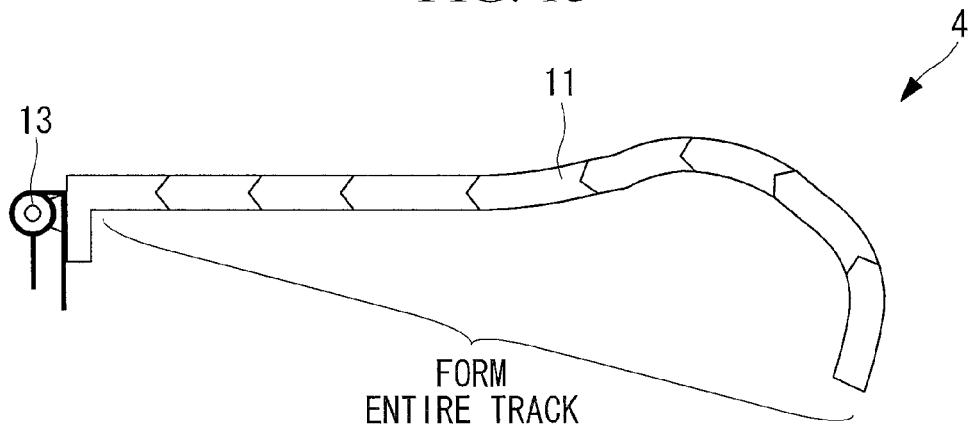
FIG. 15 is a view showing a state in which the track-forming device shown in FIG. 12 is forming the track.

Then, when the wire pulling section 13 is actuated, as shown in FIG. 11, the plurality of track-forming segmented members 11 are brought into contact with each other by the wire pulling section 13, thereby forming a three-dimensional predetermined track conforming, for example, to the internal shape of the body cavity. Thus, the insertion section 20, formed of a soft member, is deformed to conform to the shape of the track-forming device 3 of this embodiment, that is, the three-dimensional predetermined track conforming to the internal shape of the body cavity. In this state, the insertion section 20 is pushed further into the body cavity. Thus, the insertion section 20 is inserted into the body cavity along the three-dimensional predetermined track formed by the track-forming device 3 of this embodiment.

As described above, according to the track-forming device 3 of this embodiment, it is possible to insert the tubular insertion section 20 so as to conform to the internal shape of the body cavity without deforming the tissue in the body cavity. Specifically, with the track-forming device 3 of this embodiment, it is possible to form a three-dimensional insertion route (track) along which the insertion section 20 is easily inserted without imposing an excessive burden on the tissue in the body cavity and to easily insert the insertion section 20 into the body cavity along this insertion route.

Third Embodiment

Next, a track-forming device according to a third embodiment of the present invention will be described below mainly with reference to FIGS. 12 to 29. A track-forming device 4 of this embodiment will be described below mainly in terms of the differences from the track-forming device 1 of the first embodiment, identical symbols are assigned to similarities, and a description thereof will be omitted.

As shown in FIGS. 12 to 15, in the track-forming device 4 of this embodiment, the track-forming segmented members 11 are brought into contact sequentially starting from the base end, thus forming a predetermined track. A specific structure of the track-forming device 4 of this embodiment will be described below.

Figure 16:
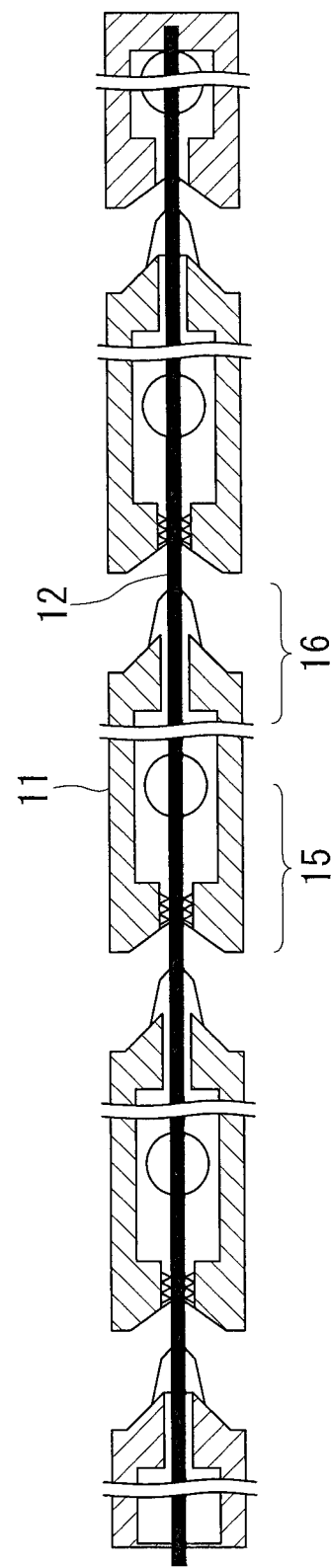
FIG. 16 is a longitudinal sectional view of the track-forming device shown in FIG. 12.

In the track-forming device 4 of this embodiment, as shown in FIG. 16, each of the track-forming segmented members 11 has, at a base end portion thereof, a wire locking unit 15 that locks the wire 12 and has, at a distal end portion thereof, a wire unlocking unit 16 that unlocks the wire 12 by being engaged with the wire locking unit 15 of the adjacent track-forming segmented member 11.

Note that, in the track-forming device 4 of this embodiment, a weak mooring device (mooring wire) (not shown) may be provided in order to prevent rotation of the track-forming segmented member 11 about the axis.

FIG. 17(a) is a front view of the track-forming segmented member 11 when viewed from the base end. FIG. 17(b) is a longitudinal sectional view of the track-forming segmented member 11. FIG. 17(c) is a front view of the track-forming segmented member 11 when viewed from the distal end. FIG. 18 is a sectional view along the line A-A' of FIG. 17(c). FIG. 19 is a sectional view along the line B-B' of FIG. 17(c).

Figure 17:
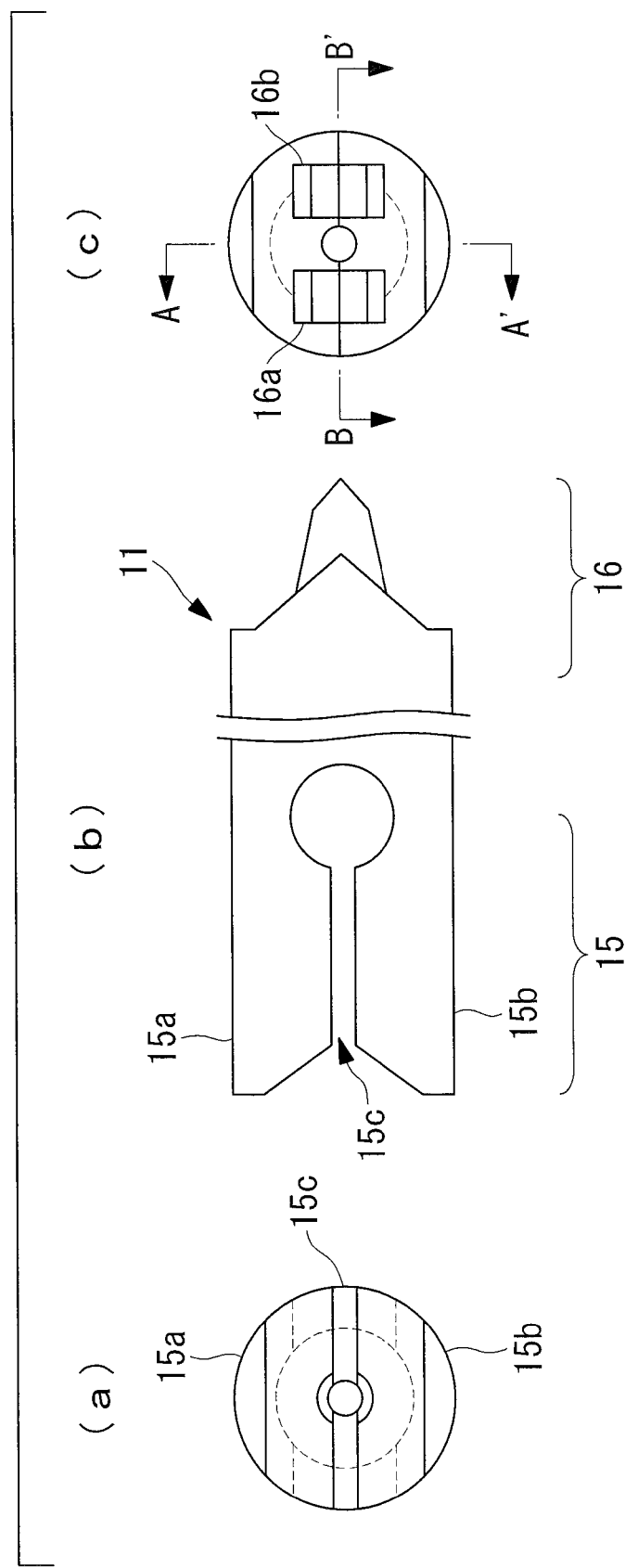
FIG. 17 includes views showing, in partially enlarged form, each of the track-forming segmented members shown in FIG. 12, where
Figure 18:
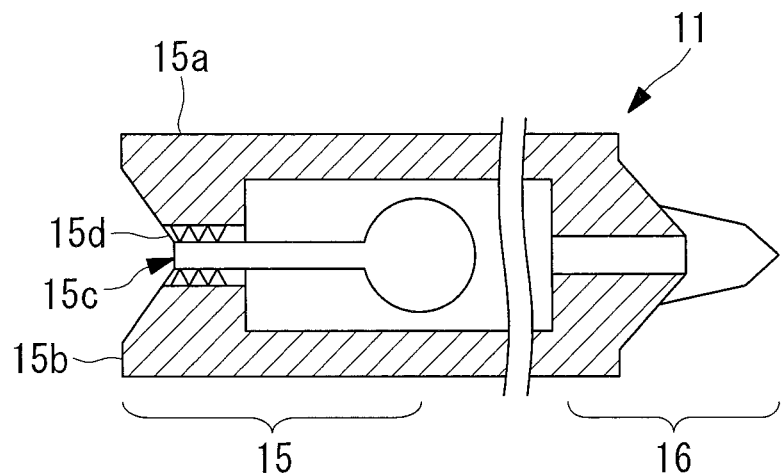
FIG. 18 is a sectional view along the line A-A' of FIG. 17(c).
Figure 19:
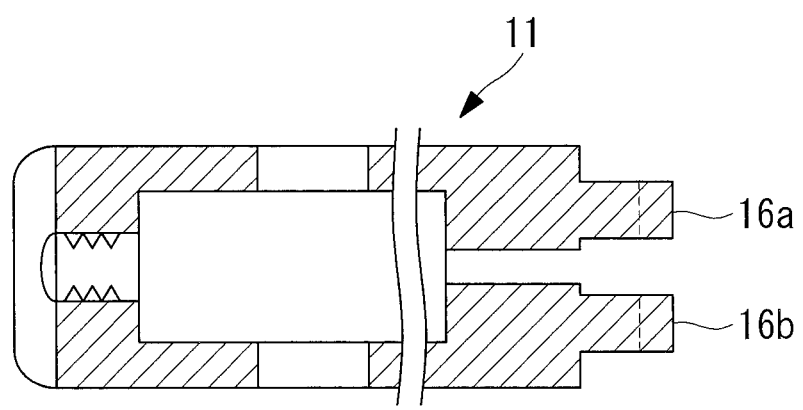
FIG. 19 is a sectional view along the line B-B' of FIG. 17(c).
Figure 20:
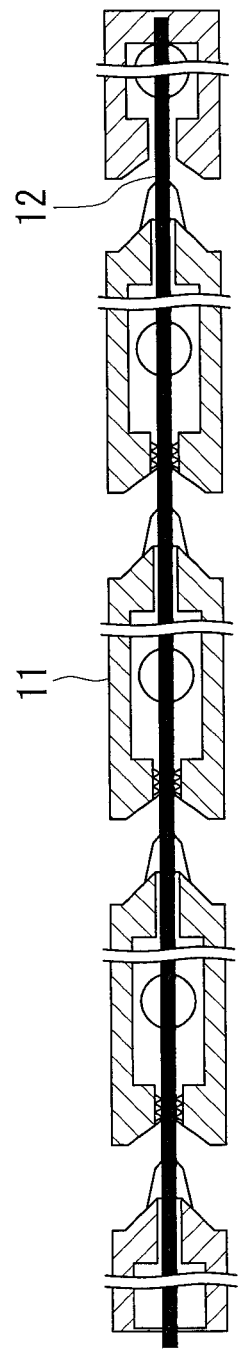
FIG. 20 is a longitudinal sectional view showing a contact state of the track-forming segmented members shown in FIG. 12 when a track is formed.
Figure 21:
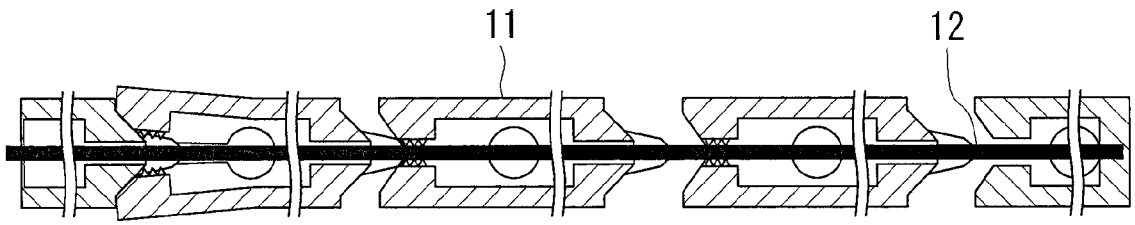
FIG. 21 is a longitudinal sectional view showing the contact state of the track-forming segmented members shown in FIG. 12 when the track is formed.
Figure 22:
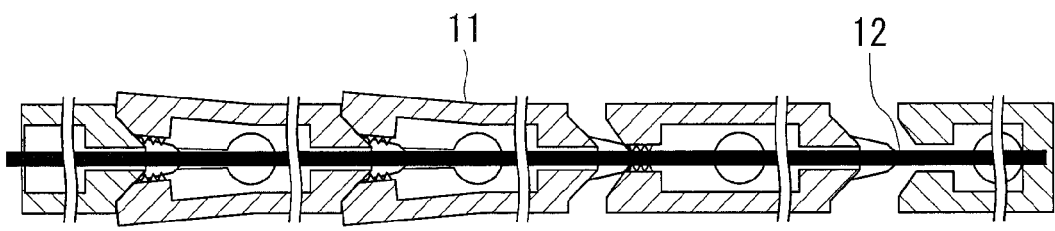
FIG. 22 is a longitudinal sectional view showing the contact state of the track-forming segmented members shown in FIG. 12 when the track is formed.
Figure 23:
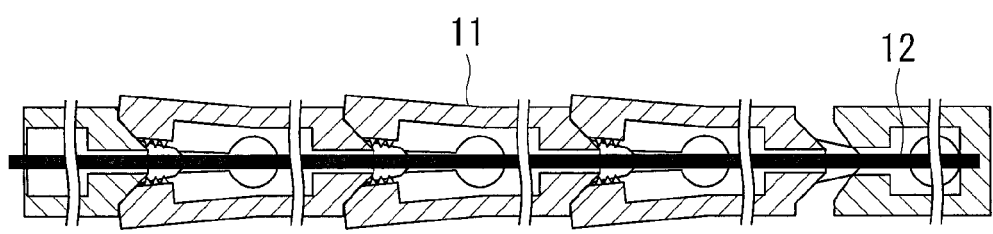
FIG. 23 is a longitudinal sectional view showing the contact state of the track-forming segmented members shown in FIG. 12 when the track is formed.
Figure 24:
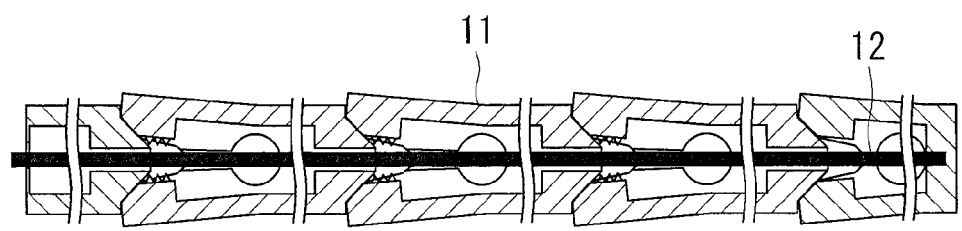
FIG. 24 is a longitudinal sectional view showing the contact state of the track-forming segmented members shown in FIG. 12 when the track is formed.
Figure 25:
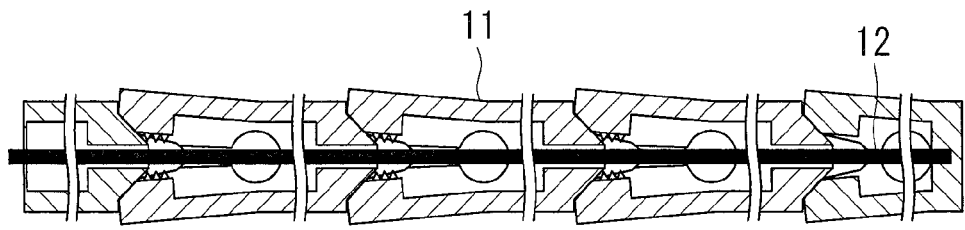
FIG. 25 is a longitudinal sectional view showing a contact state of the track-forming segmented members shown in FIG. 12 when the track is released.
Figure 26:
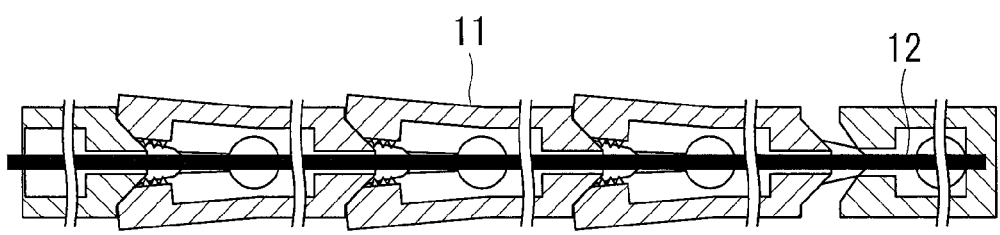
FIG. 26 is a longitudinal sectional view showing the contact state of the track-forming segmented members shown in FIG. 12 when the track is released.
Figure 27:
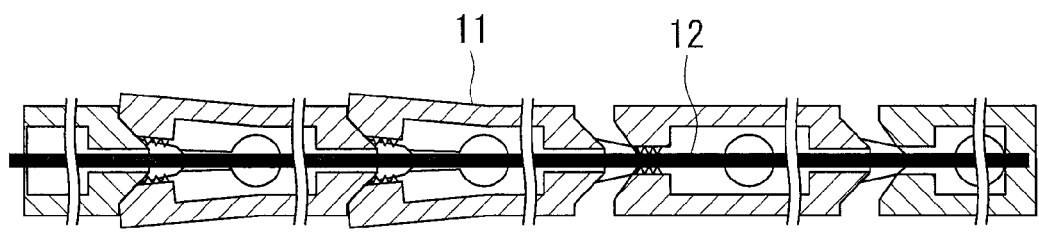
FIG. 27 is a longitudinal sectional view showing the contact state of the track-forming segmented members shown in FIG. 12 when the track is released.
Figure 28:
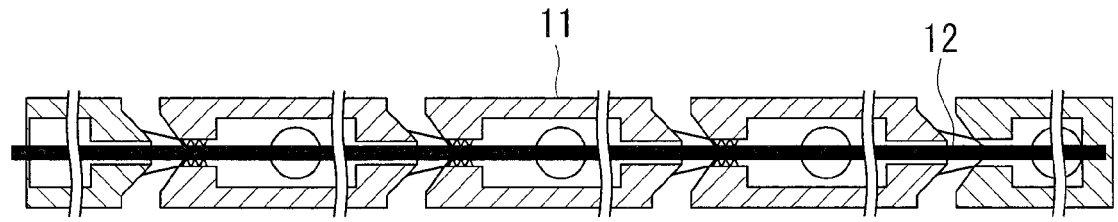
FIG. 28 is a longitudinal sectional view showing the contact state of the track-forming segmented members shown in FIG. 12 when the track is released.

As shown in FIG. 17 to FIG. 19, the wire locking unit 15 has a pair of split portions 15a and 15b that are split so as to be centered on the hole into which the wire 12 is inserted. A groove 15c that is formed in a radial direction of the track-forming segmented member 11 is provided between the split portion 15a and the split portion 15b. Furthermore, convex portions 15d that grip the wire 12 are formed on the opposing faces of the split portions 15a and 15b.

With this structure, the wire locking unit 15 locks the wire 12 in a manner such that the wire 12 is pinched radially-inward from above and below in FIG. 17(a), by the elastic forces of the split portions 15a and 15b, and the convex portions 15d, which are formed on the opposing faces of the split portions 15a and 15b, grip the wire 12.

As shown in FIG. 17 to FIG. 19, the wire unlocking unit 16 has a pair of projection portions 16a and 16b that are split so as to be centered on the hole into which the wire 12 is inserted. The projection portions 16a and 16b are each formed so as to be tapered toward the tip thereof. The projection portions 16a and 16b are fitted into the groove 15c, which is formed between the split portion 15a and the split portion 15b of the wire locking unit 15.

With this structure, the wire unlocking unit 16 releases the lock on the wire 12 performed by the wire locking unit 15, in a manner such that, when the track-forming segmented members 11 are brought into contact with each other, the projection portions 16a and 16b push open the groove 15c of the wire locking unit 15 of the adjacent track-forming segmented member 11.

Here, in the track-forming device 4 of this embodiment, the locking forces of the wire locking units 15 of the track-forming segmented members 11 that are located closer to the base end are set smaller than the locking forces of the wire locking units 15 of the track-forming segmented members 11 that are located closer to the distal end.

With this structure, as shown in FIGS. 20 to 24, when the soft wire 12 inserted into all the track-forming segmented members 11 is pulled toward the base end by the wire pulling section 13, the lock on the wire 12 can be released sequentially starting from the wire locking unit 15 of the track-forming segmented member 11 located closest to the base end. Thus, as shown in FIGS. 12 to 15, the track-forming segmented members 11 are brought into contact sequentially starting from the base end, thereby making it possible to form a predetermined track conforming, for example, to the internal shape of the body cavity. By forming the track sequentially starting from the base end in this way, the ease of insertion of the tubular insertion section 20 into the body cavity can be improved.

Note that, in the track-forming device 4 of this embodiment, in order to return the track-forming device 4 to the soft state by releasing the predetermined track formed as described above, as shown in FIGS. 25 to 28, the wire 12 is loosened by the wire pulling section 13, thereby releasing the engagement of the wire locking units 15 and the wire unlocking units 16 sequentially starting from the track-forming segmented member 11 that is located closest to the distal end, whose wire locking unit 15 has a larger locking force. Thus, the track-forming device 4 is returned to the soft state sequentially starting from the track-forming segmented member 11 that is located closest to the distal end.

Next, an operation performed when the insertion section 20 is inserted into a pericardial cavity by using the track-forming device 4 of this embodiment will be described below. Here, a description will be given of an example case in which the insertion section 20 of the endoscope is inserted into the pericardial cavity.

Figure 29:
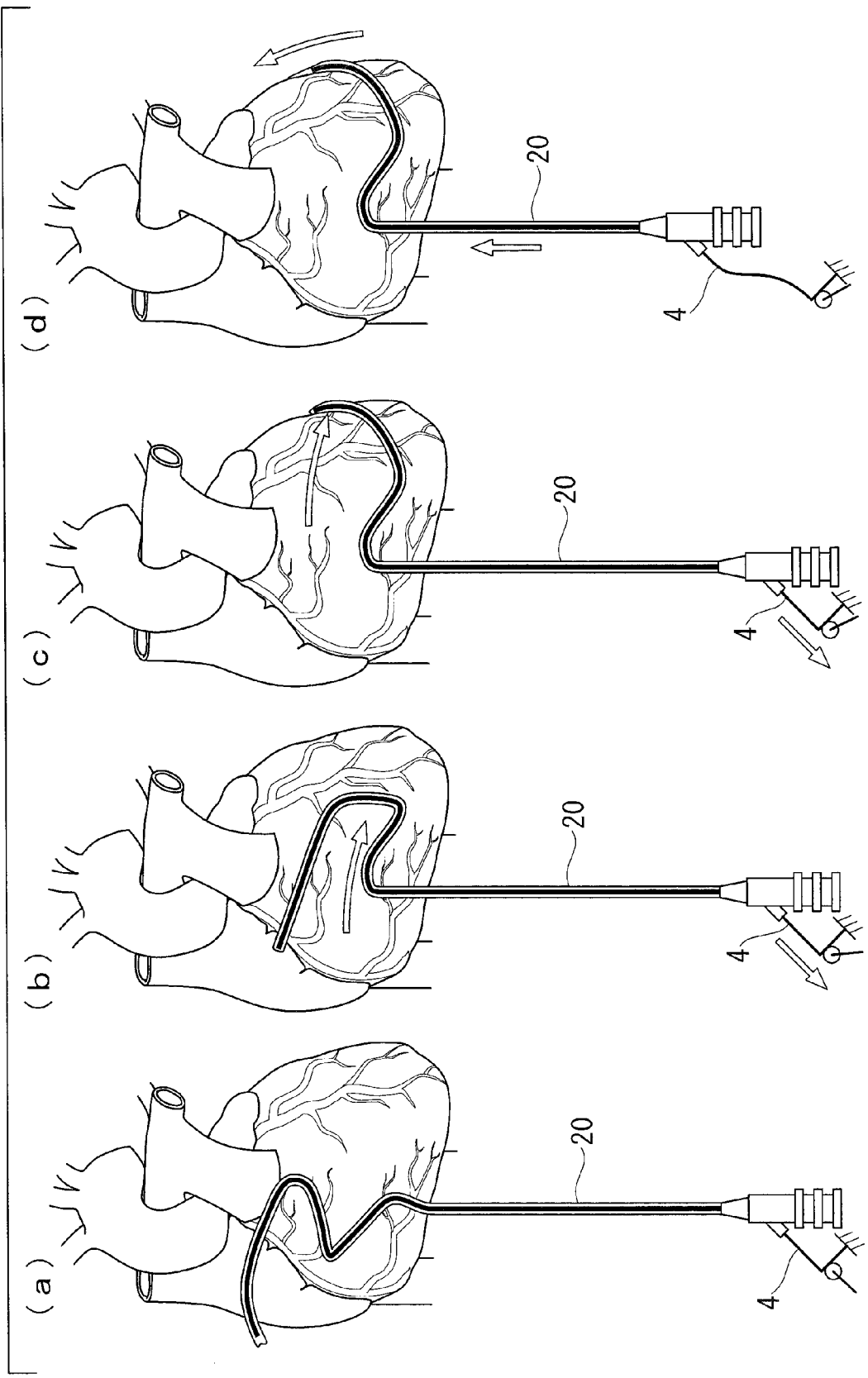
FIG. 29 includes views showing states in which the insertion section is inserted into a pericardial cavity by using the track-forming device shown in FIG. 12, where

FIGS. 29(*a*) to 29(*d*) are views showing the flow of insertion of the insertion section 20 of the endoscope to an observation/treatment target site located at the posterior side of the heart.

First, as shown in FIG. 29(*a*), in order to approach the posterior side of the heart, the insertion section 20 is inserted into the vicinity of the right atrium. At this time, the insertion section 20 is disposed in a space between the pericardium and the heart. In this state, the track-forming device 4 is in the soft state, the position of the insertion section 20 is unfixed, and the insertion section 20 is lightly brought into contact with the organ.

Next, as shown in FIG. 29(*b*), the track-forming device 4 forms a track starting from the hand side (the base end). In the state shown in FIG. 29(*b*), the hand side is directed toward the left atrium. In this state, an insertion route is determined starting from the hand side. At this time, the distal end portion is still lightly brought into contact with the organ.

Next, as shown in FIG. 29(*c*), the track is further sequentially formed, thus-forming an appropriate route to the posterior side. In this state, the insertion route is determined starting from the hand side. At this time, the distal end portion is still in the soft state and is lightly brought into contact with the organ.

Next, as shown in FIG. 29(*d*), by making the track-forming device 4 form the track, the route to the posterior side of the heart is ensured, and the insertion section 20 itself is further inserted. In this state, because an appropriate insertion route is fixed, the insertion section 20 can be easily moved forward.

As described above, according to the track-forming device 4 of this embodiment, when the soft wire 12 inserted into all the track-forming segmented members 11 is pulled toward the base end by the wire pulling section 13, the track-forming segmented members 11 can be brought into contact with each other sequentially starting from the base end, thus forming a predetermined track. By forming the track sequentially starting from the base end in this way, the ease of insertion of the tubular insertion section 20 into the body cavity can be improved.

Modification

Figure 30:
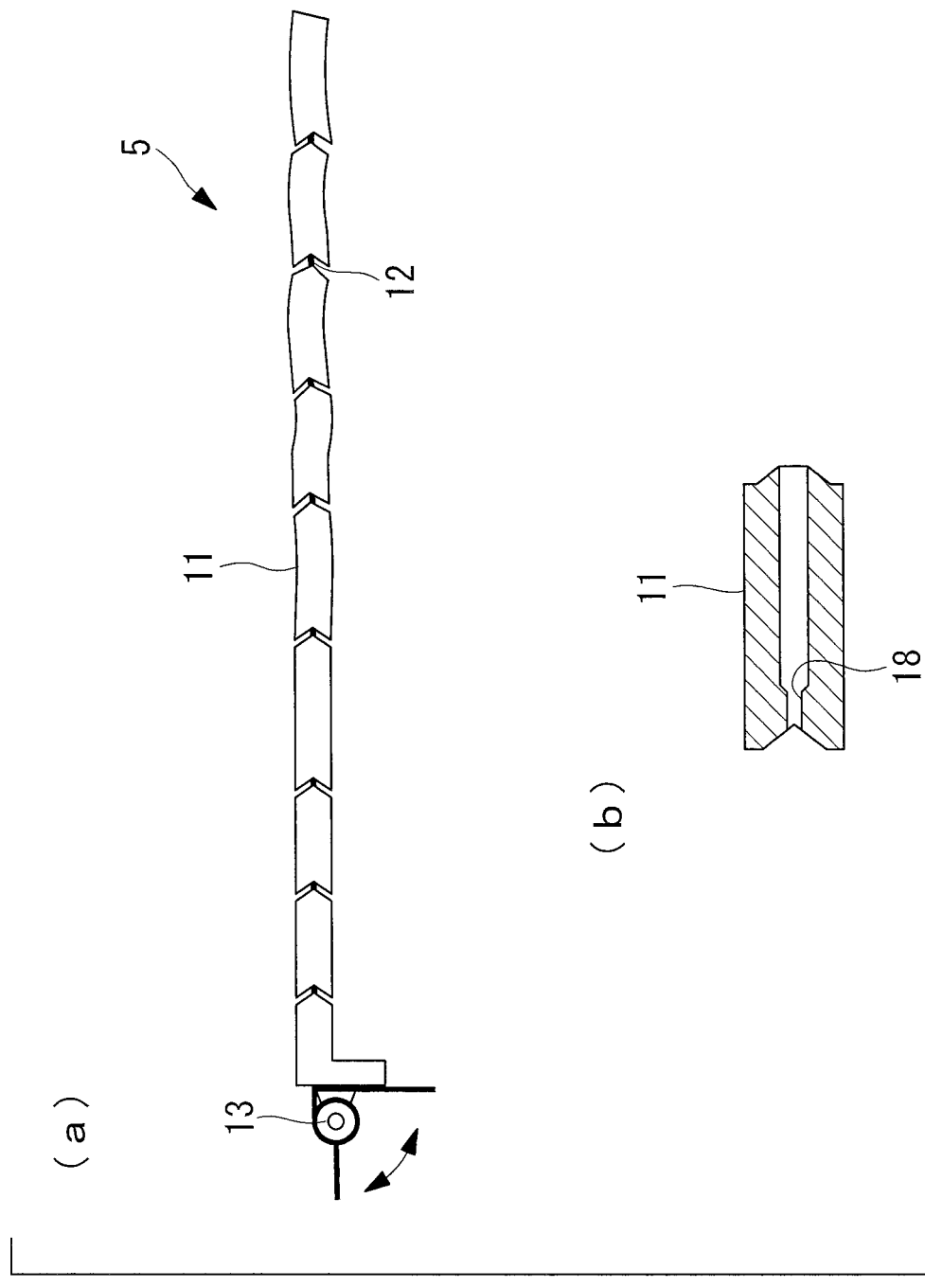
FIG. 30 includes views showing a modification of the track-forming device shown in FIG. 12, where
Figure 31:
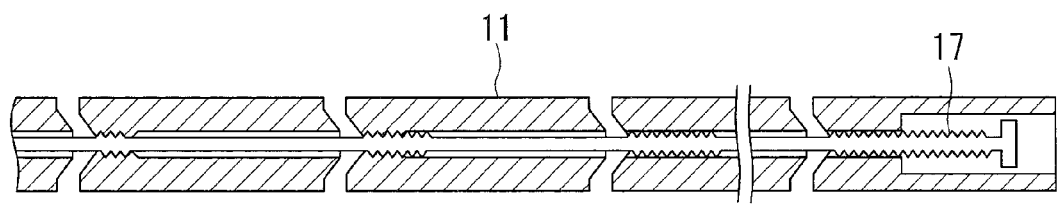
FIG. 31 is a longitudinal sectional view showing the track-forming device shown in FIG. 30.

As a modification of the track-forming device 4 of this embodiment, as shown in FIGS. 30 and 31, external thread portions 17 may be formed at predetermined positions on the wire 12, and internal thread portions 18 to be engaged with the external thread portions 17 may be formed on internal sides of the track-forming segmented members 11.

Figure 32:
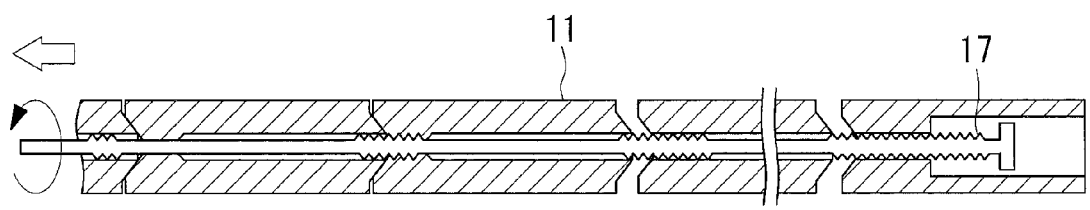
FIG. 32 is a longitudinal sectional view showing a contact state of the track-forming segmented members shown in FIG. 30 when a track is formed.
Figure 33:
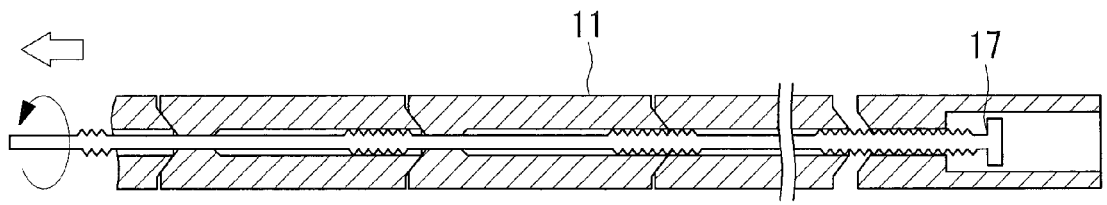
FIG. 33 is a longitudinal sectional view showing the contact state of the track-forming segmented members shown in FIG. 30 when the track is formed.

According to a track-forming device 5 of this modification, having the above-described structure, as shown in FIGS. 32 and 33, when the soft wire 12 inserted into all the track-forming segmented members 11 is rotated about the axis, the external thread portions 17 formed at the predetermined positions on the wire 12 can be engaged with the internal thread portions 18 formed on the internal sides of the track-forming segmented members 11, thus bringing the plurality of track-forming segmented members 11 into contact with each other and forming a predetermined track conforming, for example, to the internal shape of the body cavity.

Furthermore, in the track-forming device 5 of this modification, the external thread portions 17 that are located closer to the base end of the wire 12 are formed shorter in the longitudinal direction than the external thread portions 17 that are located closer to the distal end.

With this structure, when the soft wire 12 inserted into all the track-forming segmented members 11 is rotated about the axis, the track-forming segmented members 11 can be brought into contact with each other sequentially starting from the base end, thus forming a predetermined track. By forming the track sequentially starting from the base end in this way, the ease of insertion of the insertion section 20 into the body cavity can be improved.

Fourth Embodiment

Next, a track-forming device according to a fourth embodiment of the present invention will be described below mainly with reference to FIGS. 34 to 37. A track-forming device 6 of this embodiment will be described below mainly in terms of the differences from the track-forming device 1 of the first embodiment, identical symbols are assigned to similarities, and a description thereof will be omitted.

Figure 34:
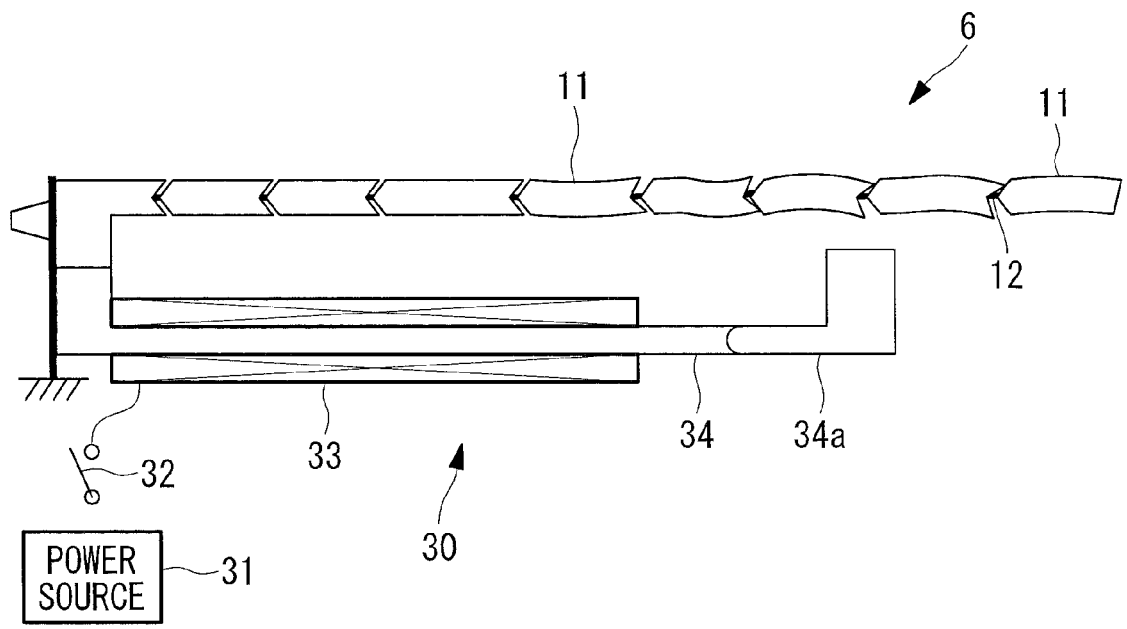
FIG. 34 is a side view of a track-forming device according to a fourth embodiment of the present invention (soft state).

As shown in FIG. 34, the track-forming device 6 of this embodiment is provided with a magnetic force generator (contacting section) 30 that brings the plurality of track-forming segmented members 11 into contact with each other in the longitudinal direction due to a magnetic force, instead of the wire pulling section 13 of the track-forming device 1 of the first embodiment.

The magnetic force generator 30 is formed of a power source 31, a switch 32, a magnetic flux applying section 33, and a magnetic flux transferring section 34.

The magnetic flux transferring section 34 is a bar-like member disposed parallel to the plurality of track-forming segmented members 11, is made of a high-permeability magnetic material, and transfers magnetic flux generated in the magnetic flux applying section 33 to the plurality of track-forming segmented members 11. Furthermore, the magnetic flux transferring section 34 has a bent portion 34*a* that is bent to be aligned with the track formed by the track-forming segmented members 11.

The magnetic flux applying section 33 is a coil wound in the circumferential direction of the magnetic flux transferring section 34 and, when an electric current is supplied from the power source 31 by closing the switch 32, generates magnetic flux in a direction perpendicular to the electric current, that is, in the axial direction of the magnetic flux transferring section 34 (right-hand rule).

Note that, in this embodiment, the track-forming segmented members 11 are made of a high-permeability magnetic material.

The operation of the track-forming device 6 of this embodiment, having the above-described structure, will be described below.

As shown in FIG. 34, in the track-forming device 6 of this embodiment, while the magnetic force generator 30 is not actuated, the plurality of track-forming segmented members 11 that are arranged in the longitudinal direction with spaces therebetween are connected by the soft wire 12 so as to be able to be curved. In this state, when the track-forming device 6 of this embodiment is inserted into the insertion section 20, the track-forming device 6 can be inserted into the insertion section 20 so as to conform to the shape of the insertion section 20. In this state, the insertion section 20 is inserted into the body cavity. Because both the insertion section 20 and the track-forming device 6 of this embodiment can be curved in this state, the insertion section 20 and the track-forming device 6 are inserted into the body cavity while deforming to conform to the internal shape of the body cavity.

Figure 35:
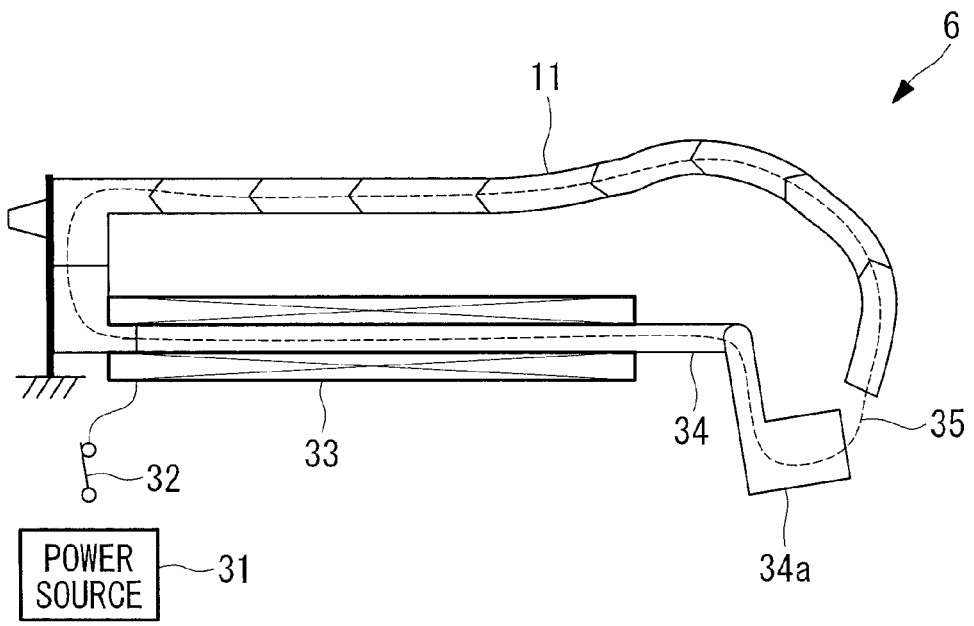
FIG. 35 is a side view of the track-forming device shown in FIG. 34 (track forming state).

In this state, the switch 32 of the magnetic force generator 30 is closed, thereby supplying an electric current from the power source 31 to the magnetic flux applying section 33. Thus, as shown in FIG. 35, magnetic flux generated in the magnetic flux applying section 33 forms a magnetic flux loop 35 passing from the distal end of the track-forming segmented members 11 to the base end thereof via the magnetic flux transferring section 34. Thus, the plurality of track-forming segmented members 11 are brought into contact with each other due to the magnetic force, thus forming a predetermined track conforming, for example, to the internal shape of the body cavity.

Thus, the insertion section 20, formed of the soft member, is deformed to conform to the shape of the track-forming device 6 of this embodiment, that is, a predetermined track conforming to the internal shape of the body cavity. In this state, the insertion section 20 is pushed further into the body cavity. Thus, the insertion section 20 is inserted into the body cavity along the predetermined track formed by the track-forming device 6 of this embodiment.

As described above, according to the track-forming device 6 of this embodiment, a predetermined track conforming to the internal shape of the body cavity can be formed in a non-contact manner by using the magnetic force generator 30. Furthermore, the weight of the device can be reduced. Furthermore, as in the above-described embodiments, it is possible to insert the tubular insertion section 20 so as to conform to the internal shape of the body cavity without deforming the tissue in the body cavity. Specifically, with the track-forming device 6 of this embodiment, it is possible to form an insertion route (track) along which the insertion section 20 is easily inserted without imposing an excessive burden on the tissue in the body cavity and to easily insert the insertion section 20 into the body cavity along this insertion route.

Modification

Figure 36:
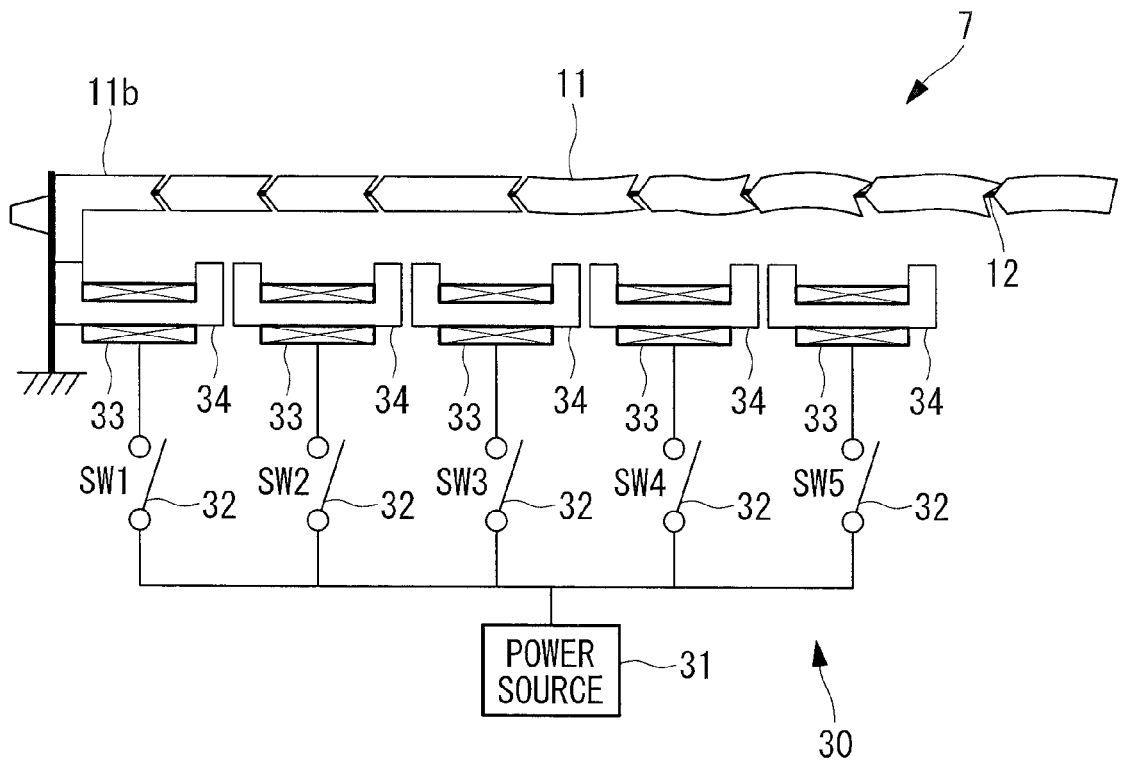
FIG. 36 is a side view of a modification of the track-forming device shown in FIG. 34 (soft state).
Figure 37:
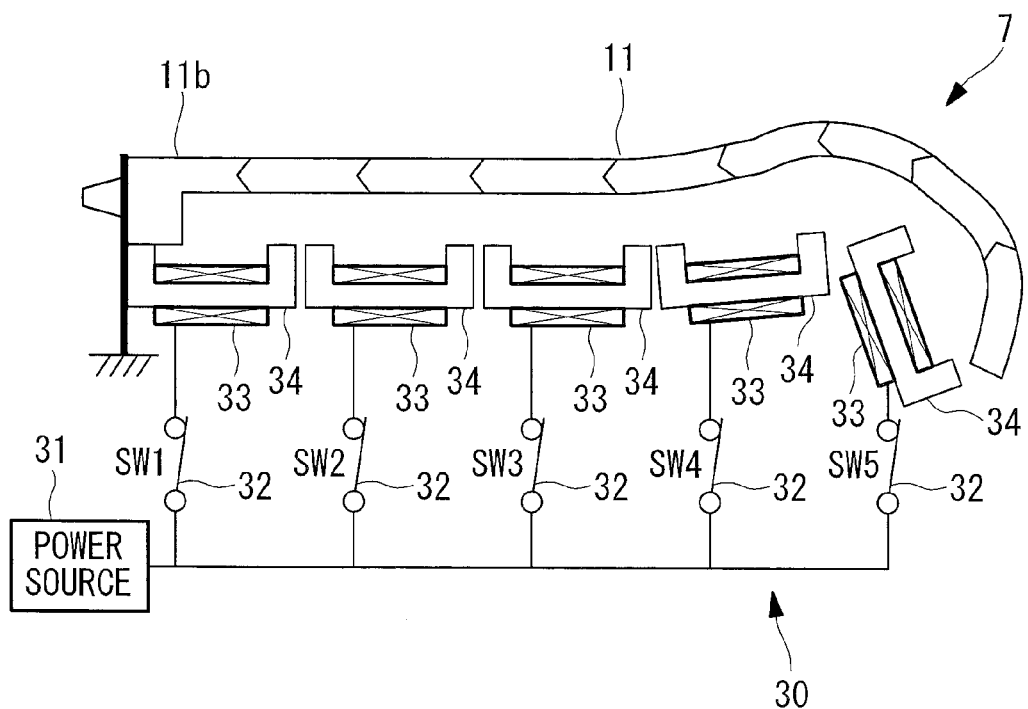
FIG. 37 is a side view of the track-forming device shown in FIG. 36 (track forming state).

As a modification of the track-forming device 6 of this embodiment, as shown in FIGS. 36 and 37, a plurality of magnetic flux applying sections 33 may be provided.

In a track-forming device 7 according to this modification, the plurality of magnetic flux applying sections 33 are arranged parallel to the plurality of track-forming segmented members 11.

According to the track-forming device 7 of this modification, at a portion where a track is to be formed, a magnetic flux loop can be formed by supplying an electric current to the magnetic flux applying sections 33, thus bringing the plurality of track-forming segmented members 11 into contact with each other due to the magnetic force and forming a predetermined track conforming, for example, to the internal shape of the body cavity.

Specifically, by sequentially closing the switches 32 starting from the switch 32 that is located at the base end (SW1 in the figure), the track-forming segmented members 11 can be brought into contact sequentially starting from the base end, thus forming a predetermined track conforming to the internal shape of the body cavity. By forming the track sequentially starting from the base end in this way, the ease of insertion of the tubular insertion section 20 into the body cavity can be improved.

Although the embodiments and the modifications of the present invention have been described above in detail with reference to the drawings, the specific structures are not limited to those of the embodiments, and design changes that do not depart from the scope of the present invention are also encompassed. For example, the present invention can be applied to an embodiment in which the above-described embodiments and modifications are appropriately combined.

Reference Signs List 1, 2, 3, 4, 5, 6, 7 track-forming device
11 track-forming segmented members
12 wire (connecting member)
13 wire pulling section (contacting section)
15 wire locking unit
16 wire unlocking unit
17 external thread portions
18 internal thread portions
20 insertion section
21 distal-end bending portion
22 flexible portion
23 operating portion
30 magnetic force generator (contacting section)
31 power source
32 switch
33 magnetic flux applying section
34 magnetic flux transferring section

The invention claimed is:

1. A track-forming device that forms an insertion route in a body cavity for insertion of one of a soft endoscope and a soft sheath into the body cavity, the track-forming device comprising:
a plurality of track-forming segmented members that are arranged in a longitudinal direction with spaces therebetween;
a soft connecting member that connects the plurality of track-forming segmented members; and
a contacting section that brings the plurality of track-forming segmented members into contact with each other in the longitudinal direction,
wherein, when the plurality of track-forming segmented members are brought into contact with each other by the contacting section, a predetermined track is formed,
the connecting member is a soft wire that is inserted into all the track-forming segmented members in the longitudinal direction and that is secured to one of the track-forming segmented members that is located at a distal end;

the contacting section is a wire pulling section that pulls the wire toward a base end, and each of the track-forming segmented members has, at one end portion thereof, a wire locking unit that locks onto the wire and has, at the other end portion thereof, a wire unlocking unit that unlocks the wire locking portion from the wire by being engaged with the wire locking unit of an adjacent one of the track-forming segmented members.

2. A track-forming device according to claim 1, wherein tapers having predetermined angles are formed on contact faces of the track-forming segmented members.

3. A track-forming device according to claim 1, wherein locking forces of the wire locking units of the track-forming segmented members that are located closer to the base end are set smaller than locking forces of the wire locking units of the track-forming segmented members that are located closer to the distal end.

* * * * *